(12) United States Patent
Habersetzer et al.

(10) Patent No.: US 10,864,062 B2
(45) Date of Patent: Dec. 15, 2020

(54) PROCESS FOR PREPARING A BODY HAVING AN OSSEOINTEGRATIVE TOPOGRAPHY FORMED ON ITS SURFACE

(71) Applicant: STRAUMANN HOLDING AG, Basel (CH)

(72) Inventors: Philippe Habersetzer, Basel (CH); Simon Berner, Basel (CH); Christoph Appert, Basel (CH)

(73) Assignee: STRAUMANN HOLDING AG, Basel (CH)

( * ) Notice: Subject to any disclaimer, the term of this patent is extended or adjusted under 35 U.S.C. 154(b) by 458 days.

(21) Appl. No.: 15/730,253

(22) Filed: Oct. 11, 2017

(65) Prior Publication Data

US 2018/0104026 A1  Apr. 19, 2018

(30) Foreign Application Priority Data

Oct. 13, 2016  (EP) .................................. 16 193 726

(51) Int. Cl.
| | |
|---|---|
| *A61C 8/00* | (2006.01) |
| *A61L 27/06* | (2006.01) |
| *C04B 41/50* | (2006.01) |
| *C04B 41/00* | (2006.01) |
| *C04B 41/53* | (2006.01) |
| *C04B 41/87* | (2006.01) |
| *C04B 111/00* | (2006.01) |

(52) U.S. Cl.
CPC ............ *A61C 8/0012* (2013.01); *A61C 8/005* (2013.01); *A61L 27/06* (2013.01); *C04B 41/5042* (2013.01); *A61L 2400/18* (2013.01); *C04B 41/009* (2013.01); *C04B 41/5353* (2013.01); *C04B 41/87* (2013.01); *C04B 2111/00836* (2013.01)

(58) Field of Classification Search
CPC ....... A61C 8/0012; A61C 8/005; A61L 27/06; A61L 2400/18; C04B 41/5042; C04B 41/009; C04B 41/5353; C04B 41/87; C04B 2111/00836
See application file for complete search history.

(56) References Cited

U.S. PATENT DOCUMENTS

| | | | | |
|---|---|---|---|---|
| 6,033,582 | A * | 3/2000 | Lee ..................... | A61L 27/3839 204/192.32 |
| 6,702,855 | B1 * | 3/2004 | Steinemann ........ | A61F 2/30767 623/23.53 |
| 2004/0049287 | A1 * | 3/2004 | Descouts ............. | A61C 8/0012 623/23.6 |

(Continued)

OTHER PUBLICATIONS

Mar. 14, 2017 Extended Search Report issued in European Patent Application No. 16 19 3726.

*Primary Examiner* — Nicholas D Lucchesi
(74) *Attorney, Agent, or Firm* — Oliff PLC

(57) ABSTRACT

A process for preparing a body having an osseointegrative topography formed on its surface. The process includes the steps of providing a primary body made of a titanium-zirconium alloy containing 13 to 17 wt-% of zirconium, sandblasting the primary body, and etching the sandblasted primary body with an etching solution including hydrochloric acid, sulfuric acid and water at a temperature of above 80° C. to obtain the body, said etching being performed for a duration of 350 seconds at least.

17 Claims, 2 Drawing Sheets

(56) References Cited

U.S. PATENT DOCUMENTS

Figure 1:
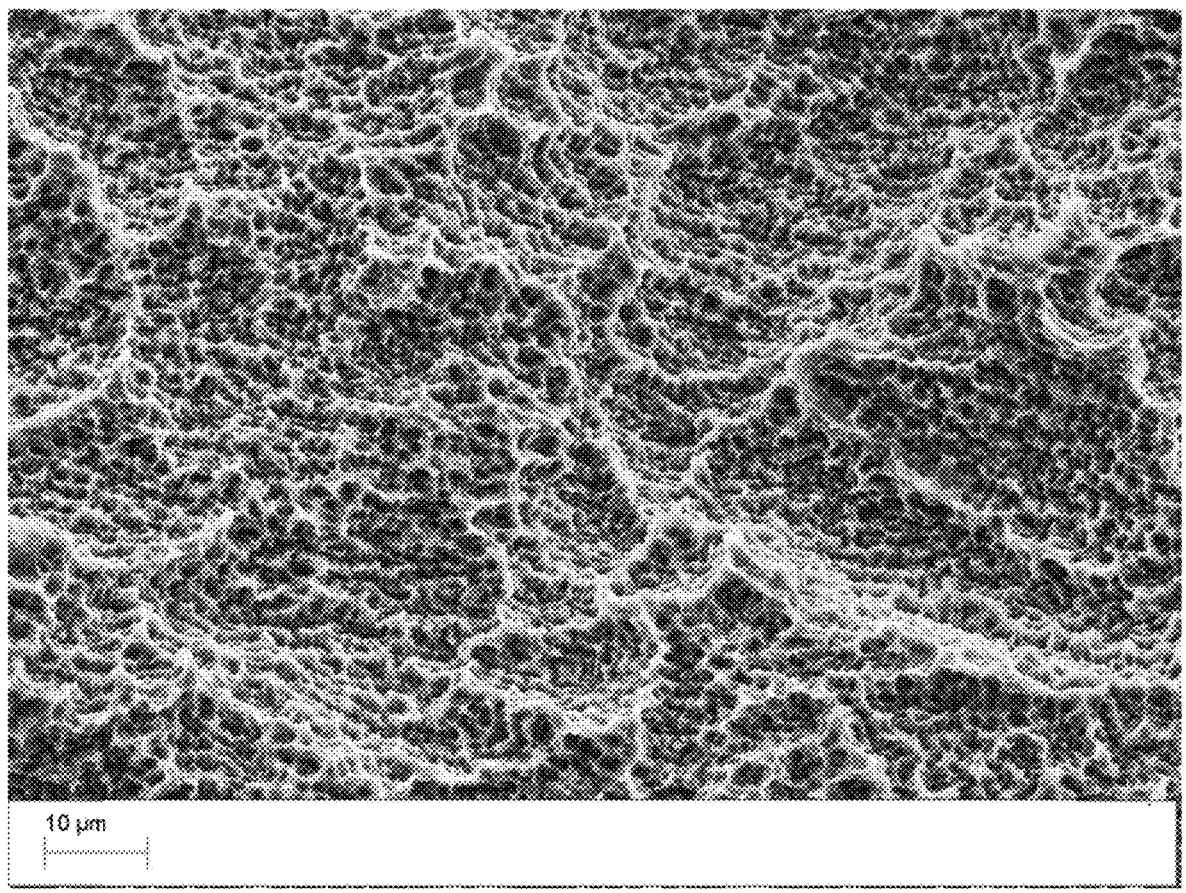

| | | | |
|---|---|---|---|
| 2007/0190107 A1* | 8/2007 | Tosatti | A61L 27/34 424/423 |
| 2008/0261178 A1* | 10/2008 | Homann | A61C 8/0012 433/201.1 |
| 2009/0061506 A1* | 3/2009 | Hofer | A61B 5/14546 435/287.9 |
| 2010/0015203 A1* | 1/2010 | Tengvall | A61L 17/145 424/423 |
| 2010/0179665 A1* | 7/2010 | Schlottig | A61C 8/0012 623/23.53 |
| 2011/0233169 A1* | 9/2011 | Mayfield | A61C 8/0012 216/37 |
| 2012/0288828 A1 | 11/2012 | Robb et al. | |
| 2014/0342316 A1 | 11/2014 | Berner et al. | |
| 2015/0086943 A1 | 3/2015 | Schwarz et al. | |

\* cited by examiner

PROCESS FOR PREPARING A BODY HAVING AN OSSEOINTEGRATIVE TOPOGRAPHY FORMED ON ITS SURFACE

The present invention relates to a process for preparing a body having an osseointegrative topography formed on its surface. The present invention further relates to a body obtainable by said process, in particular to a surgical implant or a part to be fixed on a surgical implant, more particularly to a dental implant or a dental implant abutment.

Dental implants are artificial tooth roots made of a biocompatible and mechanically stable material, such as titanium or ceramics. They are inserted into the human jawbone and retained by means of osseointegration, i.e. the direct structural and functional connection between living bone and the implant's surface. Dentures, bridges or single crowns can then be attached to the dental implant, either directly or indirectly by means of an abutment, to restore the masticatory function and aesthetics.

The most common dental implants on the market are made of titanium. In order to promote a fast and strong osseointegration, the surface is preferably roughened by the so-called SLA®-technology, which includes sandblasting the implant's surface followed by acid etching.

Apart from pure titanium, titanium alloys, in particular TiZr, Ti6Al4V (TAV) or Ti6Al7Nb (TAN), have been suggested as material for dental implants, in particular in view of biofunctionality, specifically their low specific weight, their high tensile strength and their high fatigue strength.

A specifically well-suited titanium-zirconium alloy is described in WO 97/29624, said alloy comprising a zirconium content of less than 25% by weight but more than 5% by weight, and having mechanical properties superior to those of unalloyed and cold-formed titanium.

The alloy according to WO 97/29624 is hot forged and subsequently cold worked. The forging process is carried out at temperatures above 850° C. with subsequent rapid cooling of the alloy. Alternatively, the forging process may be carried out in the range of alpha/beta phase transition at 770° C. to 830° C.

WO 97/29624 further discloses that apart from titanium and zirconium, the alloy can comprise further elements, such as iron in an amount of 0.3 wt.-% at most or hafnium in an amount of 0.5 wt.-% at most. Further developments of the technology described in WO 97/29624 have surprisingly shown that by adding iron as an alloy component to the material, outstandingly high mechanical properties can be achieved. In fact, the addition of iron hinders grain growth and leads to an augmentation in the strength of the alloy.

Apart from its mechanical properties, in particular its strength, also the tendency of the implant to establish a fast and strong interaction with the surrounding bone tissue is of paramount importance for successful implantation.

In view of a fast and strong osseointegration, it is desirable to provide a topography on the surface of the titanium-zirconium implant alike the known SLA® topography on titanium implants. However, regarding the differences in the microstructure of a titanium-zirconium alloy compared to pure titanium, this is not an easy task.

Commercially available alloys Ti6Al4V or Ti6Al7Nb, for example, demonstrate a duplex microstructure comprising two co-existing alpha- and beta-phases, which exhibit different etching rates. Specifically, the alpha-phase dissolves faster than beta phase, leading to enrichment of the vanadium-rich beta phase on the surface, which, in use, is in the vicinity of bone.

In order to provide a controlled and phase-oriented dissolution during etching (comparable to the SLA® treatment on titanium), a single phase structure would be desirable.

It has been found that for the high-strength titanium-zirconium alloy, a close to 100% single phase microstructure can be achieved. For this material, an SLA® like topography can be achieved by sandblasting and subsequent etching of the implant's surface.

Analysis of the titanium-zirconium surface etched according to the SLA® technology has, however, revealed that it still differs in some aspects from a titanium surface for which the same etching parameters have been applied.

Also, the amount of sandblasting material, specifically corundum, has been found to be higher after the etching step than it is the case for SLA® treated titanium-implants. This finding has been quite surprising, given the relatively high hardness of the titanium-zirconium alloy and the accompanying assumption of a reduced tendency of the sandblasting material to get stuck on the alloy surface.

Impurities are generally considered undesirable on the implants surface, not only for the reason that they lead to a change in the chemical composition of the alloy surface, but also since they have—depending on the nature of the impurities—an impact on the overall surface topography, which is one of the decisive factors for obtaining a good osseointegration of the implant.

There is therefore a high interest in treating the surface in a manner in which no or only a minimum amount of impurities is present after treatment.

In consideration of this, the object of the present invention is therefore to provide a process for preparing a body made of a titanium-zirconium alloy exhibiting particularly good mechanical properties, specifically a high strength, and having an osseointegrative topography formed on its surface, said process resulting in a surface which very closely resembles the known SLA® surfaces on titanium implants.

Specifically, the process shall allow a surface to be obtained on which the amount of residual sandblasting material is diminished.

The object of the present invention is solved by the process according to claim 1. Preferred embodiments of the process are defined in the dependent claims.

According to claim 1, the invention thus relates to a process for preparing a body having an osseeointegrative topography formed on its surface. In particular, the body is intended to be used as a surgical implant or as a part to be fixed on a surgical implant, more particularly as a dental implant or a dental implant abutment.

The process of the invention comprises the steps of
a) providing a primary body made of a titanium-zirconium alloy containing 13 to 17 wt-% of zirconium,
b) sandblasting the primary body, and
c) etching the sandblasted primary body with an etching solution comprising hydrochloric acid, sulfuric acid and water at a temperature of above 80° C. to obtain the body.

According to the invention and in distinction to the established SLA® technology for titanium implants, the etching is performed for a duration of 350 seconds at least.

As mentioned above, a body of particularly high strength can be achieved according to the present invention. In this regard, it is particularly preferred that apart from titanium and zirconium, the alloy also comprises iron as an alloy component, more particularly in an amount of less than 0.05 wt.-%.

Very much in analogy to the SLA® technology applied on titanium, the titanium-zirconium alloy is sandblasted for providing a macroroughness on the surface. The sandblasted primary body is then etched by an etching solution comprising hydrochloric acid, sulfuric acid and water at a temperature of above 80° C. Owed to the above mentioned macroscopic single phase nature of the specific alloy, the etching is structure-oriented, as it is also the case in the etching of SLA® treated titanium surfaces. There is therefore no major two-phase system exhibiting different dissolution rates for the phases and therefore resulting in accumulation of one of the phases and ultimately in an "asymmetric" topography.

During step b), some sandblasting material remains stuck in the surface, given the relatively harsh conditions that have to be applied for obtaining the desired macroroughness. The preferred blasting parameters for step b) depend on a number of factors, i.a. on the specific blasting method, the amount and nature of blasting material and the nozzle diameter. Typically, the blasting pressure used in step b) is at least about 1.5 bar.

According to the present invention, the residual sandblasting material is efficiently removed from the surface in step c). In this regard, it has surprisingly been found that for the specific etching solution and the etching temperature according to the SLA® technology, an efficient removal of the residual sandblasting material is obtained if the etching duration is set to 350 seconds at least. Without wanting to be bound by any theory, it is assumed that by the prolonged etching a deeper etching depth is reached and that loosening of the grains at this depth finally results in the breaking off of the sandblasting material from the alloy.

It has also been found that by prolonging the etching time up to at least 350 seconds, a surface can be achieved on the titanium-zirconium alloy body, which more closely resembles the known SLA® surfaces on titanium.

Ultimately, a body having a surface of the desired topography and which at the same time is free of blasting material and other residuals from the previous processing steps can thus be achieved by the present invention without requiring further cleaning procedures for removing residual sandblasting material.

It is, however, understood that the process of the present can nevertheless include a cleaning step, in particular using ultrasound cleaning and vibration.

Alternatively or additionally, a thermal shock procedure can be performed for an effective removal of particles. This procedure is based on the different thermal expansion coefficients of the respective materials: since metal contracts more at low temperatures than corundum, the thermal shock thus leads to a further loosing of the grains. In more concrete terms, the body is preferably dipped into liquid nitrogen, specifically at a temperature of about 77K.

Theoretically, prolonging the etching duration is against the established doctrine according to which a long etching duration can result in hydrogenation phenomena, which may lead to hydrogen embrittlement and, thus, to a decrease in the body's mechanical stability.

In consideration of this, the etching is preferably performed for a duration from 350 seconds to 540 seconds, more preferably from 360 seconds to 480 seconds, and most preferably from 360 seconds to 420 seconds. By restricting the upper limit of the etching duration, a substantial impact on the mechanical stability of the implant can be efficiently avoided.

As mentioned above, it is preferred that the alloy is at least in the region directly adjacent to the surface essentially in the alpha-phase, i.e. in the hexagonal-close-packed (hcp) structure. Thus, the material is in this region a single phase material essentially devoid of the beta-phase. This allows a structure-oriented etching of the surface and, ultimately, a SLA® like topography to be achieved.

It is to be noted that this embodiment encompasses alloys which thoroughly are in the alpha-phase as well as alloys which in a core region comprises some material in the beta-phase, i.e. a higher proportion of beta-phase than the region directly adjacent to the surface.

Although the process of the invention allows an efficient removal of sandblasting material adhering to the surface, it is further preferred that the sandblasting step b) is performed in a manner to reduce the amount of sandblasting material becoming stuck to the surface. This is of particular relevance with regard to the threading portion of the implant where the risk of particles getting jammed between to two crests of the thread is particularly high. In view of this, a sandblasting material of an average particle size in the range from 0.1 mm to 0.6 mm, particularly from 0.15 mm to 0.5 mm, and more particularly from 0.2 mm to 0.4 mm has been found to be particularly preferred. Specifically, $Al_2O_3$ particles having an average particle size in the range from 0.2 mm to 0.4 mm are used as sandblasting material in step b).

As mentioned, the present invention allows a surface topography to be obtained which very closely resembles the known SLA® surfaces on titanium implants. This has been most surprising, given the known finding that an SLA® topography cannot be created on the biphasic standard alloys Ti6Al7Nb and Ti6Al4V and given the further finding that by using the established SLA® technology a topography is created on the titanium-zirconium alloy, which is non-identical to the titanium SLA® topography obtained by using the same processing parameters.

Specifically, the topography obtainable by the process of the present invention can be defined by at least one of the following parameters:

i) $S_a$ being the arithmetic mean deviation of the surface in three dimensions and being in the range from 0.1 µm to 2.0 µm, preferably being in a range from 0.4 µm to 1.8 µm, more preferably from 0.8 µm to 1.7 µm, and most preferably from 0.9 µm to 1.5 µm;

ii) $S_t$ being the maximum peak to valley height of the profile in three dimensions and being in the range from 1.0 µm to 20.0 µm, preferably being in a range from 3.0 µm to 18.0 µm, more preferably from 4.5 µm to 13.0 µm, and most preferably from 6.0 µm to 12.0 µm; and/or iii) $S_{sk}$ being the skewness of the profile in three dimensions and being in the range from −0.6 to 0.6, preferably from −0.4 to 0.6, more preferably from −0.3 to 0.5.

The surface parameters are known to the skilled person and are analogue parameters for three dimensions to the parameters $R_a$, $R_t$ and $R_{sk}$, respectively, defined in EN ISO 4287 for two dimensions. Specifically, the above values relate to the values as e.g. obtainable by the WinSAM software (SAM (Surface Analysis Method) for Windows) known to the skilled person.

Alternatively or additionally to the above parameters, the topography obtainable by the process of the present invention can further be defined by:

iv) a developed surface area Sdr being in the range from 15% to 25.

By patterning the "gold standard" SLA® topography known from titanium implants on the body of the present invention made of a titanium-zirconium alloy, the body combines the outstanding mechanical properties owed to the alloy with the very high osseointegrative properties, which are at least partially owed to the topography.

As mentioned, the mechanical properties of the titanium-zirconium alloy are outstandingly good. Specifically, its tensile strength and 0.2% yield strength are in average about 17% higher than cold worked titanium. In addition, the tensile strength and 0.2% yield strength is also higher compared to the ISO standardized Ti6Al7Nb. In the context of the present invention, specifically good mechanical properties have been determined for a titanium-zirconium alloy containing zirconium in an amount from 13 to 15 wt-%.

As also mentioned above, iron is preferably contained in the alloy as an alloy component. Specifically, the amount of iron contained in the alloy according to the present invention is higher than 0.001 wt-%, preferably higher than 0.005 wt-%, more preferably higher than 0.01 wt-%. Preferably, the amount of iron is lower than 0.05 wt %.

According to a further preferred embodiment, the alloy contains less than 0.1 wt.-% hafnium. More preferably, the alloy is at least approximately devoid of hafnium. Due to the decrease in the amount of hafnium compared to conventional alloys comprising up to 0.1 wt.-% of hafnium, any issues arising from the inherent radioactivity of hafnium are circumvented by this embodiment, which further contributes to a high acceptance of the material by both the dentist and the patient.

As also mentioned above, the amount of sandblasting material adhering to the surface of the sandblasted primary body is diminished substantially, leading to a surface which is at least approximately devoid of any residual sandblasting material. The present invention is therefore in clear distinction to a process in which the sandblasting material that remains stuck after etching is solely attempted to be removed by rinsing.

Although the present invention allows an at least thorough removal of the sandblasting material stuck on the surface, it can further be preferred to treat the sandblasted primary body after step b) and prior to step c) with a pickling solution comprising hydrofluoric acid (HF) and nitric acid ($HNO_3$), whereby the native oxide layer formed on the titanium-zirconium alloy is at least partially removed. In this regard, it is further preferred that pickling is performed using a pickling solution containing 2 vol-% HF and 10 vol-% $HNO_3$ at room temperature for about seconds. This further allows to keep the etching duration below 8 minutes, more preferably below 7 minutes.

According to a further aspect, the present invention thus also relates to a process for preparing a body having an osseointegrative topography formed on its surface, the process comprising the steps of
A) providing a primary body made of a titanium-zirconium alloy containing 13 to 17 wt-% of zirconium, the alloy further containing iron as an alloy component in an amount of less than 0.05 wt-%,
B) sandblasting the primary body,
C) at least partially removing the native oxide layer formed on the titanium-zirconium alloy by treating the implant with a pickling solution comprising HF and $HNO_3$; and
D) etching the sandblasted primary body with an etching solution comprising hydrochloric acid, sulfuric acid and water.

Alternatively or additionally, the temperature of the etching solution during the entire etching is preferably higher than 80° C., more preferably higher than 90° C., in order to obtain the desired surface topography within a shorter time frame, and in particular within a time frame in which no detrimental effects on the body's mechanical stability occur.

According to a still further aspect, the present invention further relates to a process for preparing a body having an osseointegrative topography formed on its surface, the process comprising the steps of
α) providing a body made of a titanium-zirconium alloy containing 13 to 17 wt-% of zirconium, the alloy further containing iron as an alloy component in an amount of less than 0.05 wt-%,
β) sandblasting the body, and
γ) etching the sandblasted body with an etching solution comprising hydrochloric acid, sulfuric acid and water for a duration of at least 300 seconds, the temperature of the etching solution during the entire etching being higher than 80° C., preferably higher than 90° C.

According to a preferred embodiment of the invention described above as well as to the further aspect of the present invention, according to which the temperature of the etching solution during the entire etching is higher than 80° C., preferably higher than 90° C., the sandblasted primary body is pre-heated to a temperature above room temperature immediately prior to step c). Thus, the temperature drop caused by immersion of the cold implant is diminished or even eliminated, which contributes to a higher etching temperature and, ultimately, a shorter etching duration and a lower hydrogen concentration.

The body can be used both as dental or non-dental surgical implant. With regard to non-dental applications, the body can in particular be used as knee implant, hip implant or spinal implant.

According to a particularly preferred embodiment, the body is used as a dental implant or a part to be fixed to a dental implant, namely a dental implant abutment.

Owed to the outstandingly high mechanical strength of the alloy according to the present invention, the present invention allows a very high freedom in designing implants, specifically dental implants and dental implant abutments. The increased mechanical strength is of particular advantage where a limitation of the material volume is made necessary by clinical demands. In this case, the present invention allows a dental implant having a diameter of 3.5 mm or lower to still fulfil the mechanical stability requirements.

For aesthetic demands, in particular for the front teeth region, the present invention allows for abutments having a reduced volume in comparison to conventional abutments. There is, thus, less effort required to avoid dark translucency, e.g. by choosing opaque ceramic crowns, than it is the case for a more voluminous abutment.

Since the high material strength of the alloy according to the present invention allows a reduction in the thickness of the implant and abutment walls, the thread diameter of the screw for fixing the abutment to the implant can be augmented, which results in higher tightening torques and thus in an increased stiffness of the dental implant system. Ultimately, better fatigue values, and thus a positive influence on the long-term predictability is achieved.

EXAMPLES

The present invention is further illustrated by way of the following working examples.

Dental implants of a titanium-zirconium alloy containing 13 to 17 wt-% of zirconium were subjected to a sandblasting step followed by an etching step.

The sandblasting step was performed by using $Al_2O_3$ (corundum) particles as sandblasting material.

For the etching, the samples have been immersed in an etching bath comprising hydrochloric acid, sulfuric acid and water (the ratio of HCl (32%), $H_2SO_4$ (95%) and $H_2O$ being 2:1:1).

Immersion was performed for 360 seconds, before the samples were rinsed with deionized water and kept in aqueous solution for further storage.

Surface Topography

Figure 2:
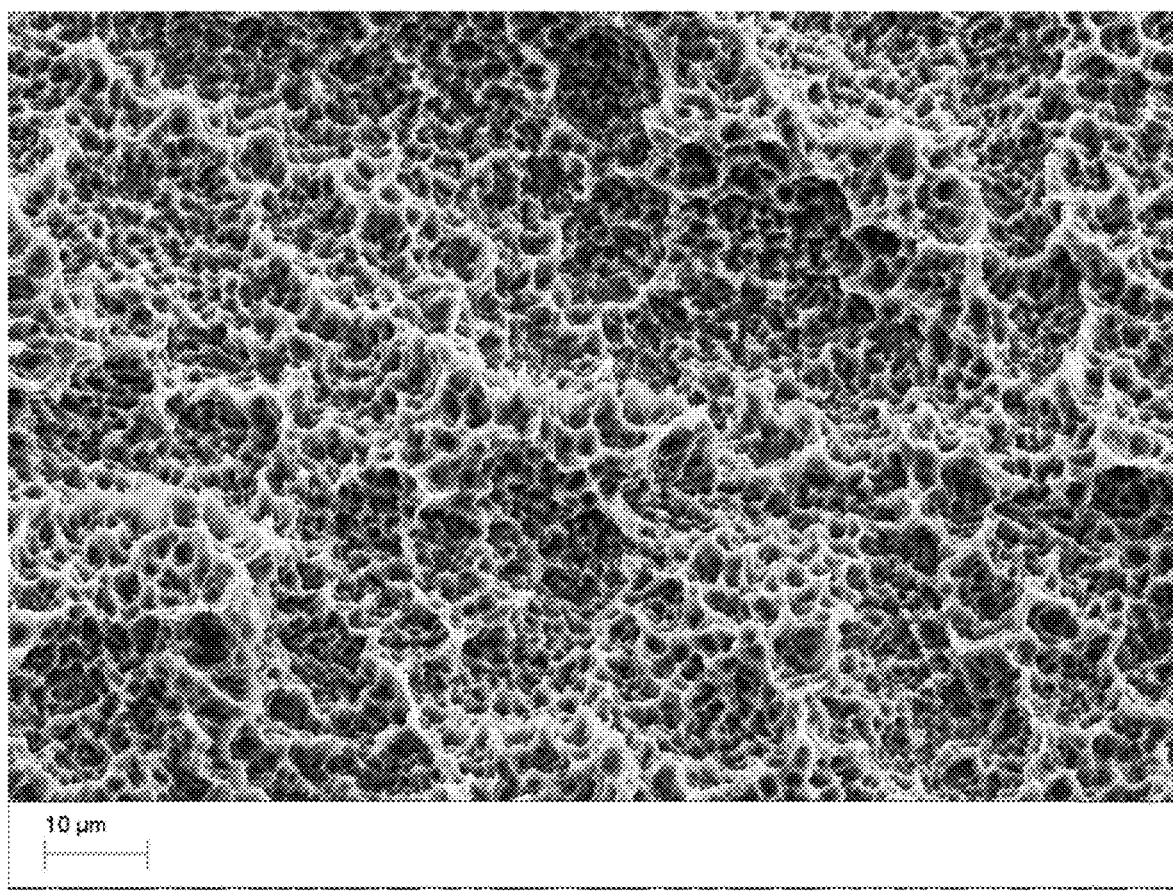

The surface topography obtained by the above treatment and its similarity to the surface topography of the well-established SLA® titanium body is illustrated by the figures, of which:

FIG. 1 shows an SEM picture of the surface of the body treated according to the present invention with a scale relating to 10 micrometer being contained in the bottom left corner; and FIG. 2 shows an SEM picture of the surface of an SLA® titanium body (for comparative reasons).

As can be seen from the figures, the sample according to the present invention shown in FIG. 1 exhibits a surface topography which very closely resembles the one of the known and established SLA® surface on titanium, shown in FIG. 2.

Residual Amount of Sandblasting Material

Further samples were analysed using energy dispersive X-ray analysis (EDX) for measuring the residual amount of sandblasting material remaining on the surface after the etching step.

In the framework of the EDX experiments, a first set of samples (samples 1) were acid etched using the etching bath mentioned above for 360 seconds, whereas a further sample (sample 2) was etched using the same etching bath, but for 300 seconds (for comparative reasons).

For the sandblasting, two batches of corundum differing in the particle size distribution and the average particle size were used: for a first sub-set of samples 1 (sample 1.1), sandblasting was performed by using corundum particles, 85% of which having a particle size from 0.21 to 0.355 mm, the average particle size thus being in a range from 0.2 mm to 0.4 mm (sand A), while for a second sub-set of samples 1 (sample 1.2) and comparative sample 2, sand comprising corundum having a larger average particle size than sand A (sand B) was used as sandblasting material.

The treatment thus led to three samples (samples 1.1, 1.2, and 2) summarized in Table 1 below:

TABLE 1

| Sample No. | 1.1 | 1.2 | 2 (comparative) |
|---|---|---|---|
| Etching duration | 360 seconds | 360 seconds | 300 seconds |
| Sandblasting material | Sand A | Sand B | Sand B |

The Al contents (wt %) detected by EDX are presented in Table 2.

TABLE 2

| Sample No. | 1.1 | 1.2 | 2.2 |
|---|---|---|---|
| Al (wt %) | 0.1 | 0.5 | 1.3 |

As can be seen from Table 2, a significant decrease in the Al content (indicative of the amount of corundum particles sticking on the surface) was revealed for samples 1.1 and 1.2 in comparison to the comparative sample 2.

As also shown in Table 2, a further decrease in the Al content and, therefore, of the residual corundum sticking to the surface was revealed for sample 1.1 that has been sandblasted with sand A having an average particle size in the range of 0.2 mm to 0.4 mm in comparison to sand B having a larger average particle size than sand A (sample 1.2).

The invention claimed is:

1. A process for preparing a body having an osseointegrative topography formed on its surface, the process comprising:
    a) providing a primary body made of a titanium-zirconium alloy containing 13 to 17 wt-% of zirconium,
    b) sandblasting the primary body, and
    c) etching the sandblasted primary body with an etching solution comprising hydrochloric acid, sulfuric acid and water at a temperature of above 80° C. for a duration in a range of from 350 to 540 seconds to obtain the body.

2. The process according to claim 1, wherein the etching is performed for a duration in a range of from 360 to 480 seconds.

3. The process according to claim 1, wherein at least in a region directly adjacent to the surface, the alloy is essentially in the alpha-phase.

4. The process according to claim 1, wherein in step b) $Al_2O_3$ particles having an average particle size in a range from 0.1 mm to 0.6 mm are used as sandblasting material.

5. The process according to claim 1, wherein the topography is defined by at least one of the following parameters:
    i) an arithmetic mean deviation of the surface ($S_a$) in three dimensions in a range of from 0.1 μm to 2.0 μm;
    ii) a maximum peak to valley height of the profile ($S_r$) in three dimensions in a range of from 1.0 μm to 20.0 μm;
    iii) a skewness of the profile ($S_{sk}$) in three dimensions in a range of from −0.6 to 0.6; and
    iv) a developed surface area (Sdr) in a range of from 15% to 25%.

6. The process according to claim 1, wherein an amount of zirconium contained in the alloy is in a range of from 13 to 15 wt-%.

7. The process according to claim 1, wherein the alloy contains iron in an amount higher than 0.001 wt-%.

8. The process according to claim 1, wherein the alloy contains an amount of iron less than 0.05 wt-%.

9. The process according to claim 1, wherein the alloy contains less than 0.1 wt.-% hafnium.

10. The process according to claim 1, wherein after step b) and prior to step c) the sandblasted primary body is treated with a pickling solution comprising hydrofluoric acid and nitric acid, whereby a native oxide layer formed on the titanium-zirconium alloy is at least partially removed.

11. The process according to claim 1, wherein the temperature of the etching solution during the entire etching is higher than 80° C.

12. The process according to claim 1, wherein the sandblasted primary body is pre-heated to a temperature above room temperature immediately prior to step c).

13. The process according to claim 1, wherein the etching is performed for a duration in a range of from 360 seconds to 420 seconds.

14. The process according to claim 1, wherein in step b) $Al_2O_3$ particles having an average particle size in a range of from 0.15 mm to 0.5 mm are used as sandblasting material.

15. The process according to claim 1, wherein in step b) $Al_2O_3$ particles having an average particle size in a range of from 0.2 mm to 0.4 mm are used as sandblasting material.

16. The process according to claim 1, wherein the topography is defined by at least one of the following parameters:
  i) an arithmetic mean deviation of the surface ($S_a$) in three dimensions in a range of from 0.4 µm to 1.8 µm;
  ii) a maximum peak to valley height of the profile ($S_r$) in three dimensions in a range of from 3.0 µm to 18.0 µm; and
  iii) a skewness of the profile ($S_{sk}$) in three dimensions in a range of from −0.4 to 0.6.

17. The process according to claim 1, wherein the alloy contains iron in an amount higher than 0.005 wt-%.

\* \* \* \* \*